(12) United States Patent
Grabowski et al.

(10) Patent No.: US 8,333,794 B2
(45) Date of Patent: Dec. 18, 2012

(54) SIDE BALLOON IDENTIFIERS AND METHODS FOR RADIAL AND AXIAL ALIGNMENT IN A CATHETER ASSEMBLY

(75) Inventors: Gerald Grabowski, Plymouth, MN (US); Adam Jennings, Buffalo Hills, MN (US); Dimitry Smelansky, Minneapolis, MN (US); Rob Lucas, Princeton, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 279 days.

(21) Appl. No.: 12/179,960

(22) Filed: Jul. 25, 2008

(65) Prior Publication Data
US 2010/0023107 A1 Jan. 28, 2010

(51) Int. Cl.
*A61F 2/06* (2006.01)
(52) U.S. Cl. ........................................ 623/1.11
(58) Field of Classification Search .......... 623/1.11, 623/1.12, 1.34–1.35; 606/191, 194; 604/101.01, 604/101.05, 103.1, 96.01
See application file for complete search history.

(56) References Cited

U.S. PATENT DOCUMENTS

| | | | |
|---|---|---|---|
| 5,591,172 A * | 1/1997 | Bachmann et al. | 623/1.11 |
| 6,146,356 A | 11/2000 | Wang et al. | |
| 6,210,429 B1 | 4/2001 | Vardi et al. | |
| 6,325,826 B1 | 12/2001 | Vardi et al. | |
| 7,118,593 B2 | 10/2006 | Davidson et al. | |
| 7,220,275 B2 | 5/2007 | Davidson et al. | |
| 7,344,557 B2 * | 3/2008 | Yadin | 623/1.11 |
| 2003/0047126 A1 * | 3/2003 | Tomaschko | 116/201 |
| 2005/0278010 A1 * | 12/2005 | Richardson | 623/1.11 |
| 2006/0229697 A1 * | 10/2006 | Gerdts et al. | 623/1.11 |
| 2008/0045896 A1 * | 2/2008 | Yribarren et al. | 604/103.1 |
| 2008/0208307 A1 * | 8/2008 | Ben-Muvhar et al. | 623/1.11 |
| 2010/0023107 A1 * | 1/2010 | Grabowski et al. | 623/1.11 |

FOREIGN PATENT DOCUMENTS

| | | |
|---|---|---|
| EP | 1512380 | 3/2005 |
| WO | 2005107643 | 11/2005 |
| WO | 2007100672 | 9/2007 |

* cited by examiner

*Primary Examiner* — Gary Jackson
*Assistant Examiner* — Amy Shipley
(74) *Attorney, Agent, or Firm* — Seager, Tufte & Wickhem, LLC

(57) ABSTRACT

A catheter assembly and related methods having a main balloon, a branch balloon arrangement and a stent. The branch balloon arrangement can include a branch balloon and at least one orientation indicator. The orientation indicator can include visible markings on portions of the side balloon or on inflation segments coupled in fluid communication to the side balloon. The side balloon can have a specific color that is different from a color of the main balloon for improved visualization of the side balloon. The orientation indicator can be helpful in aligning the side balloon relative to features of the stent. The stent can include a side branch opening located between distal and proximal open ends of the stent.

10 Claims, 6 Drawing Sheets

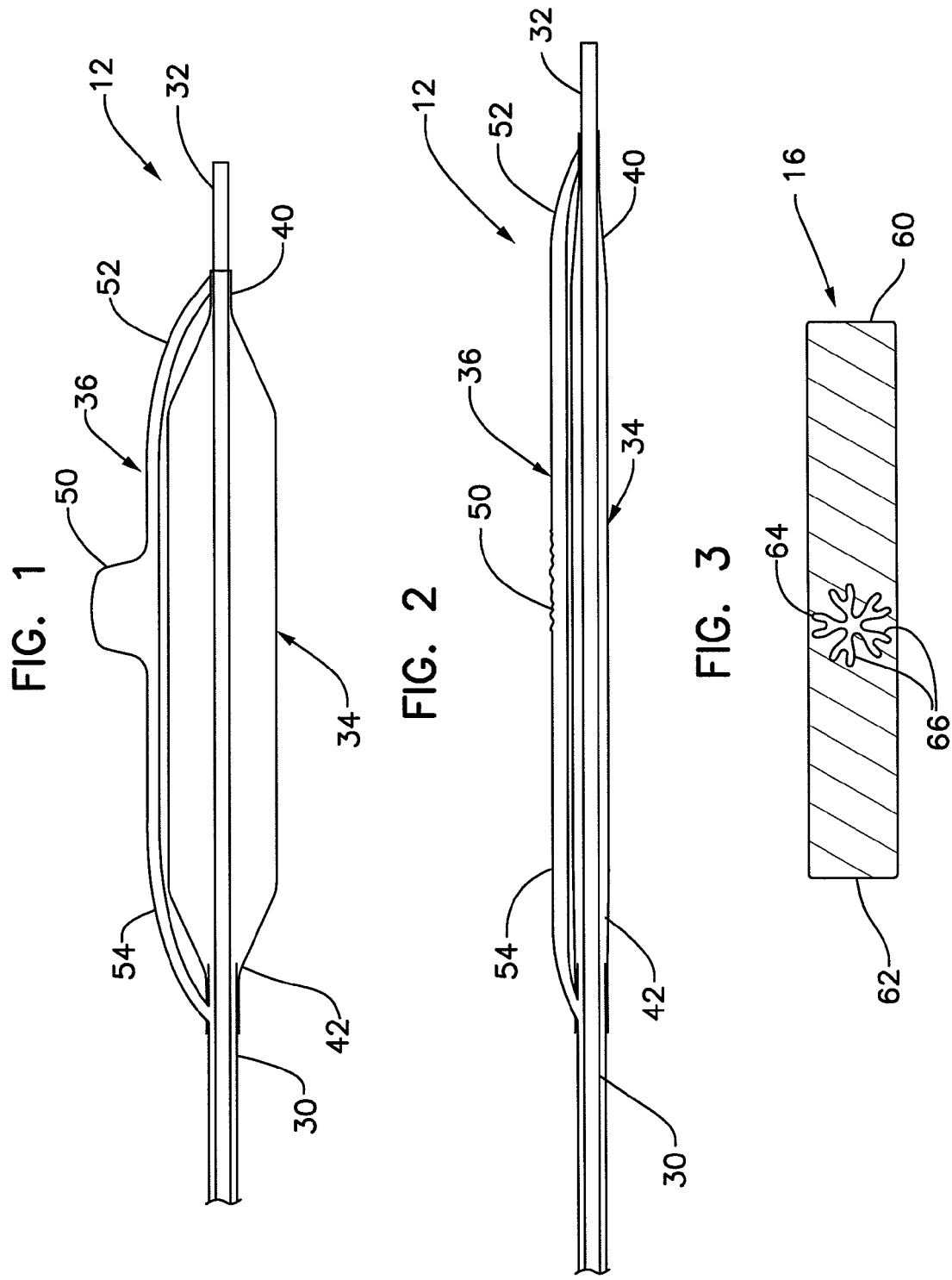

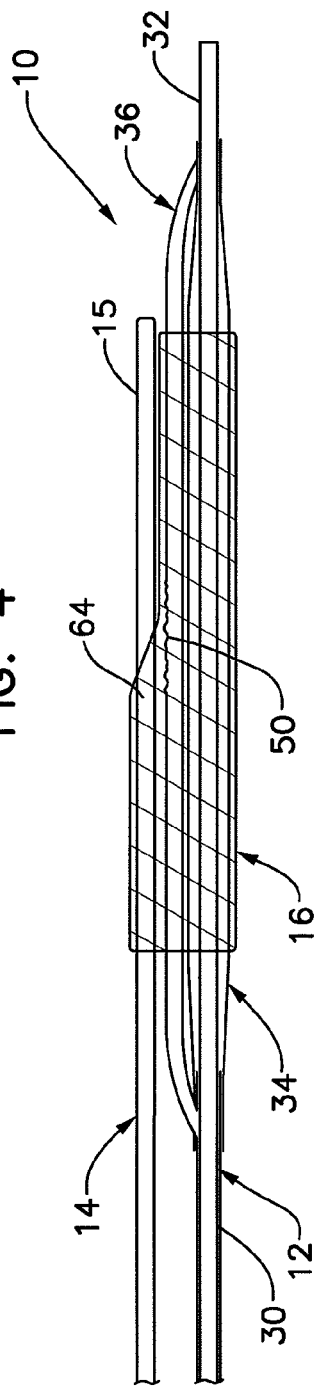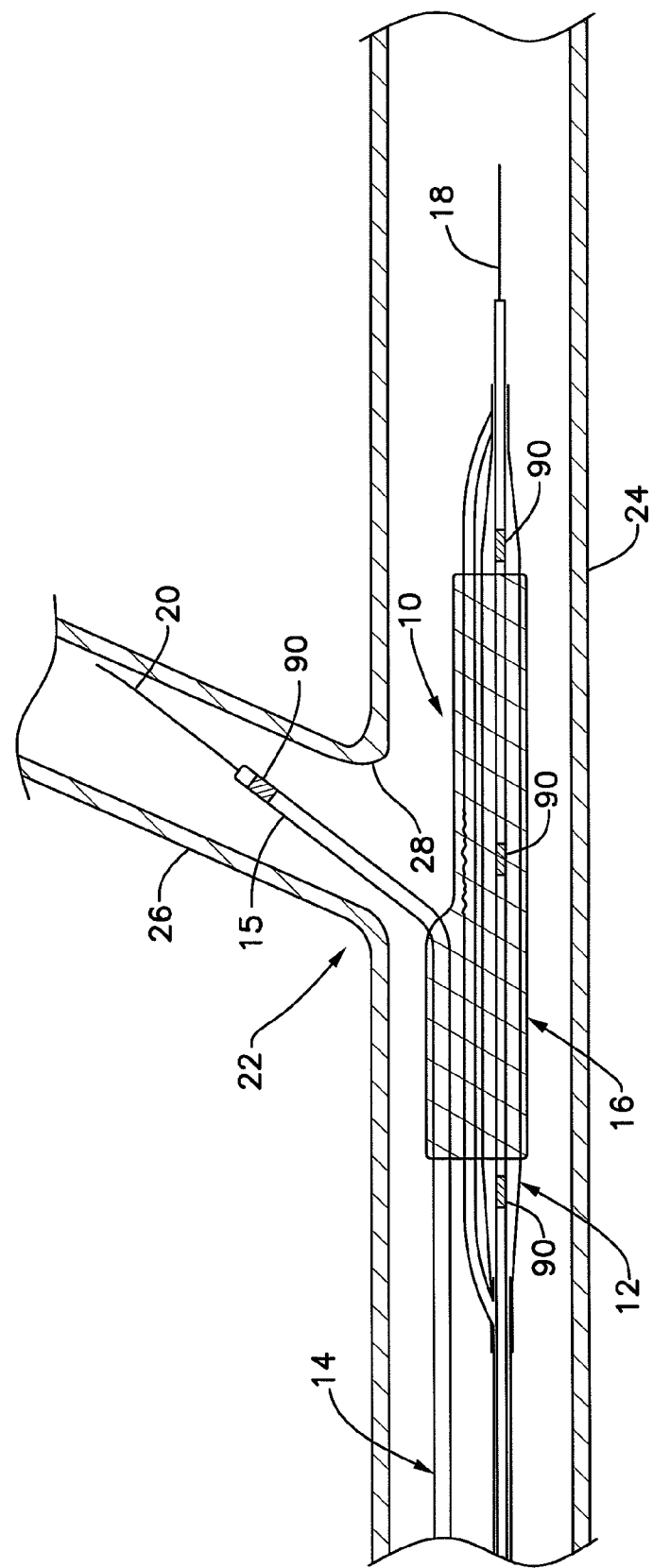

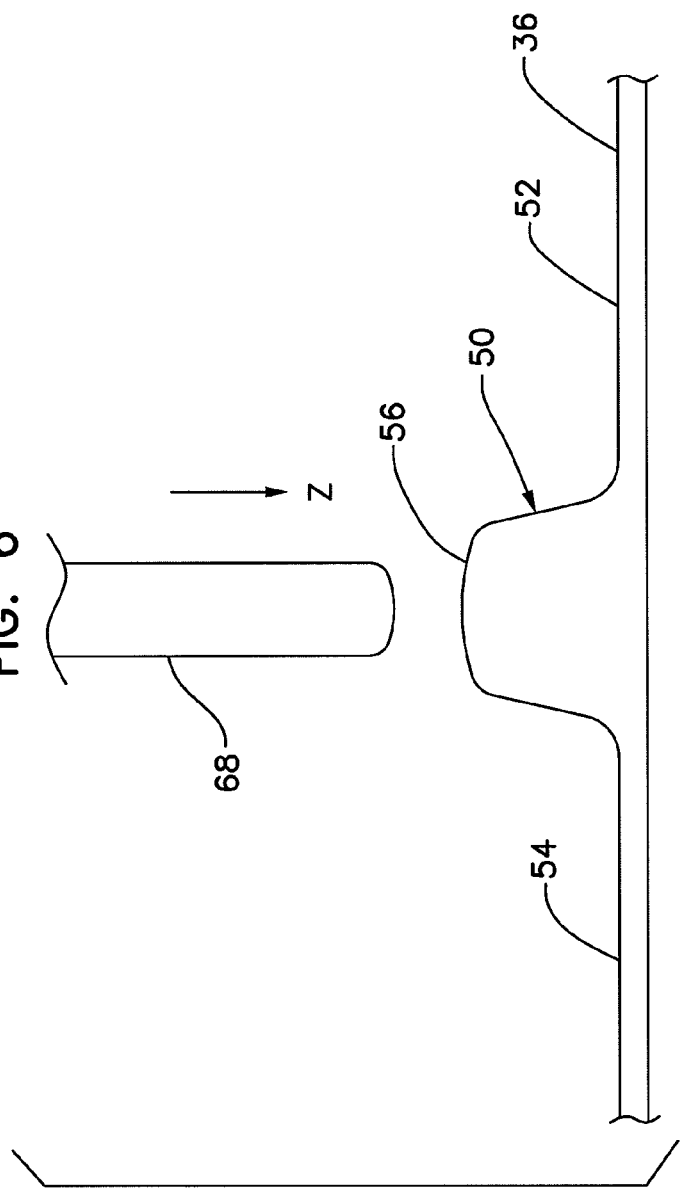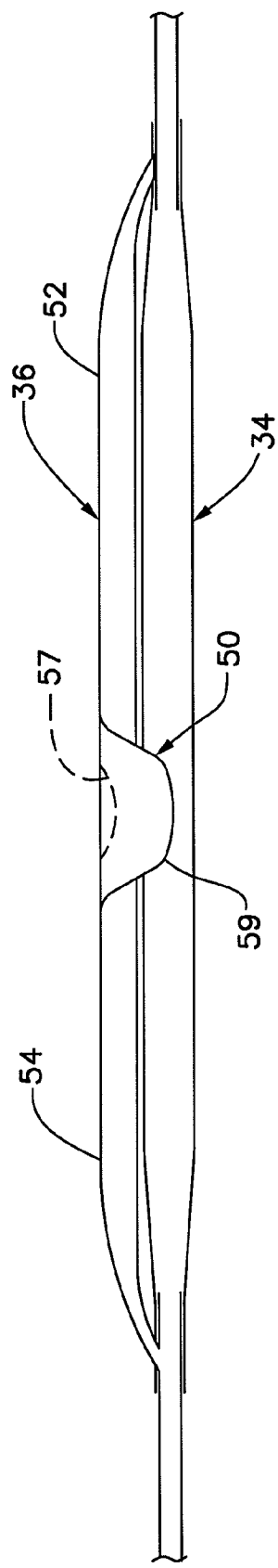

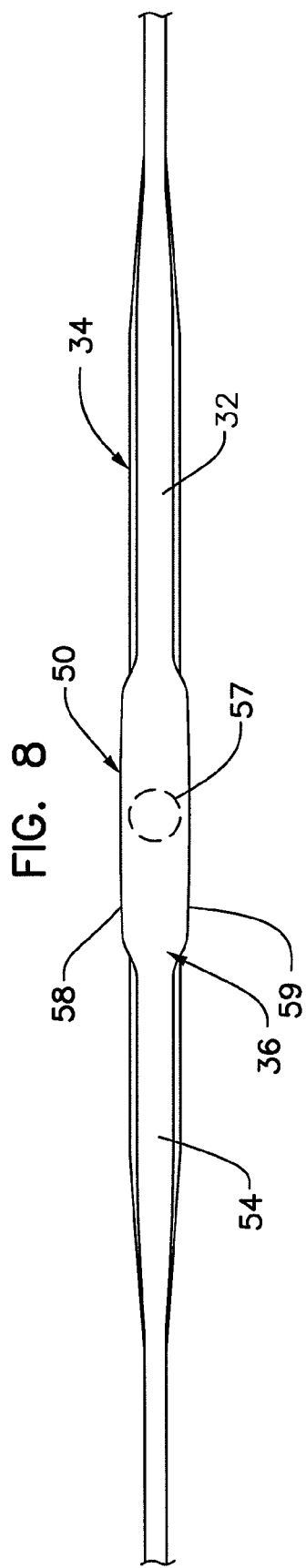
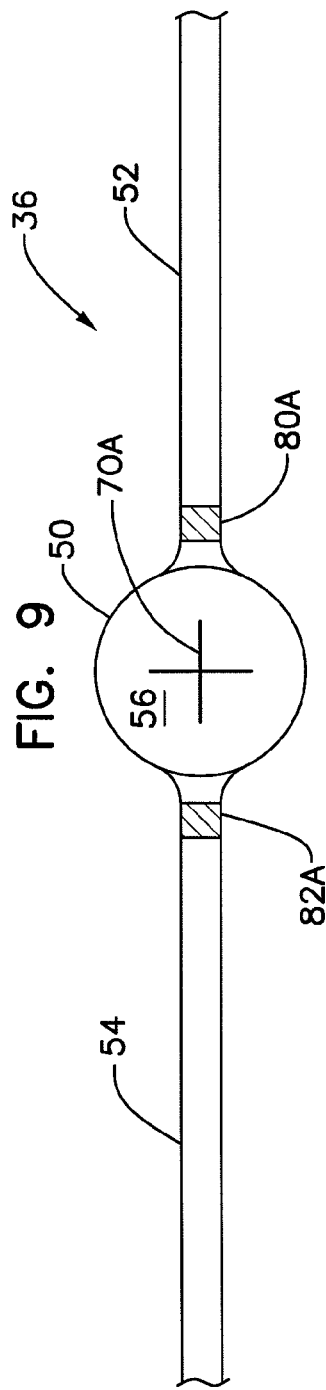
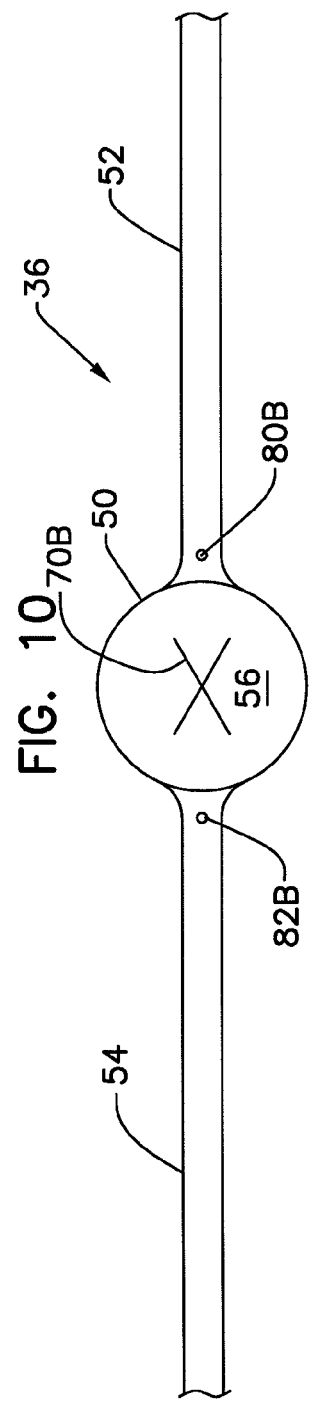

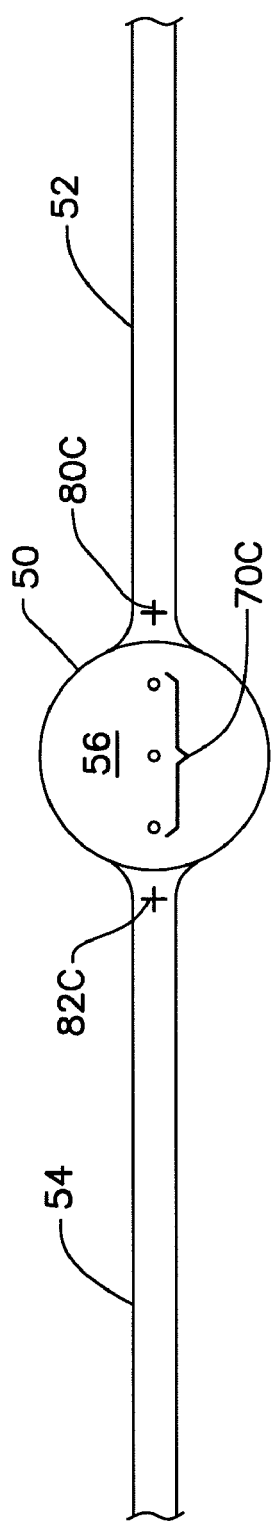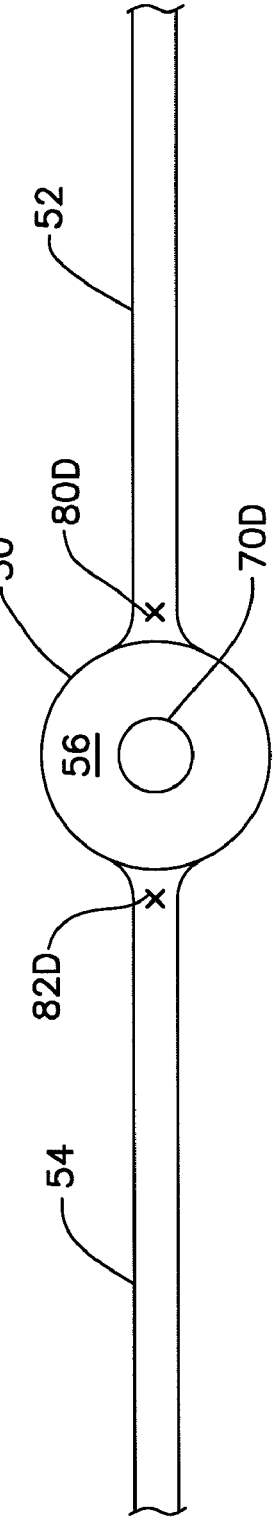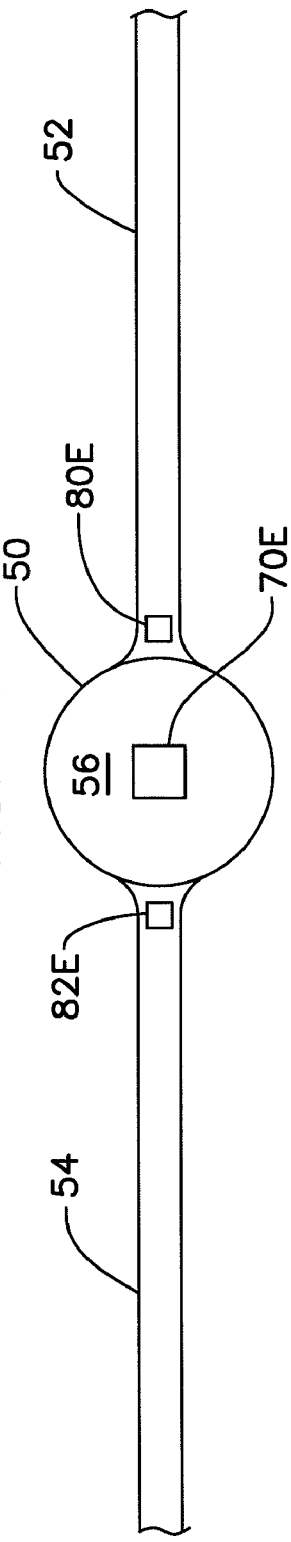

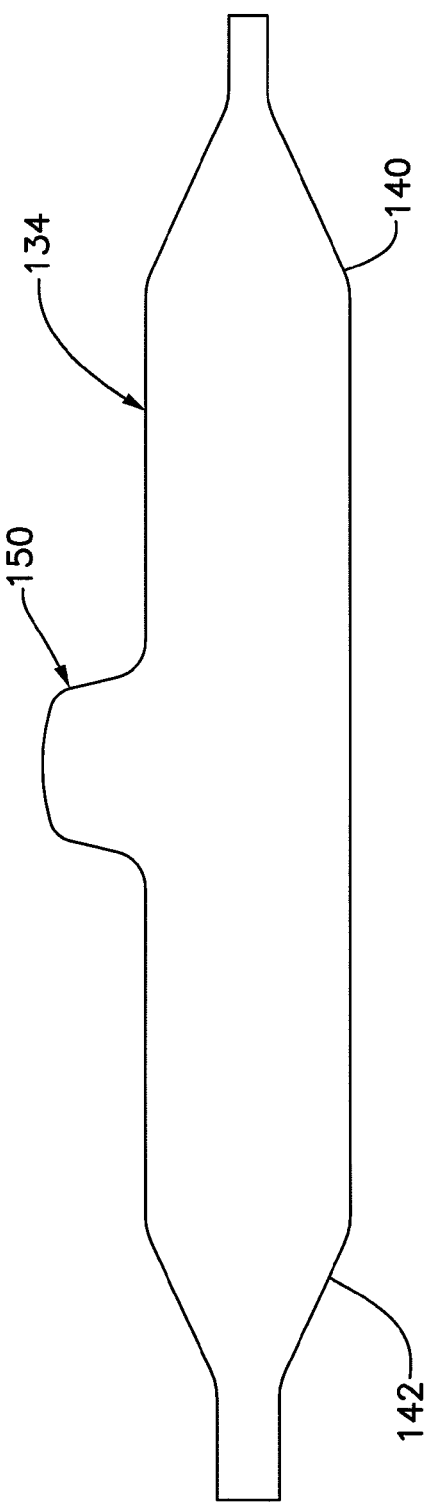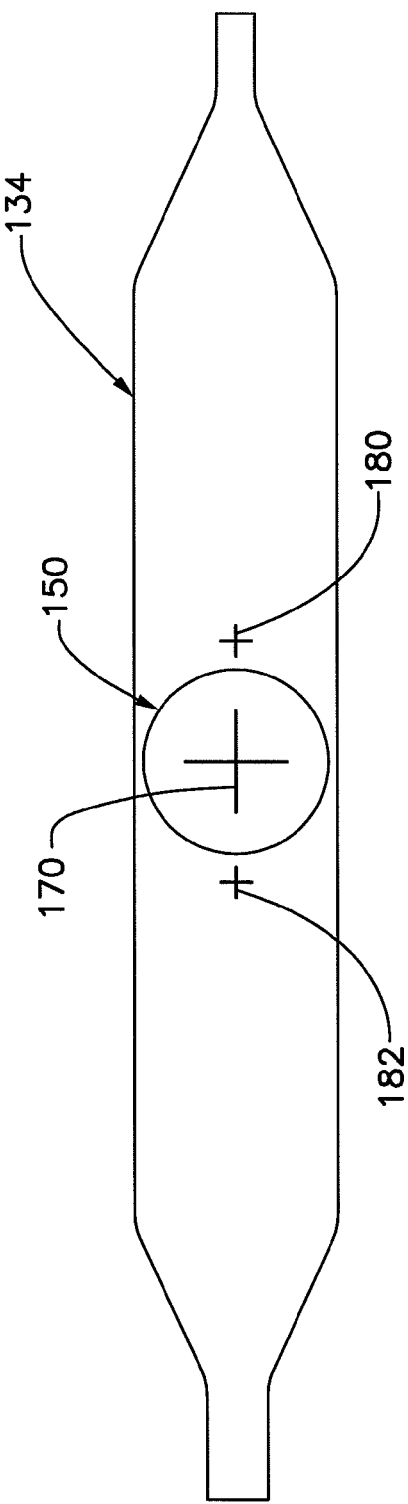

SIDE BALLOON IDENTIFIERS AND METHODS FOR RADIAL AND AXIAL ALIGNMENT IN A CATHETER ASSEMBLY

TECHNICAL FIELD

This disclosure relates to catheter assemblies configured for treatment of a vessel bifurcation.

BACKGROUND

Catheters are used with stents and inflatable structures to treat conditions such as strictures, stenoses, and narrowing in various parts of the body. Various catheter designs have been developed for the dilatation of stenoses and to deliver and deploy stents at treatment sites within the body.

Stents are typically intraluminally placed by a catheter within a vein, artery, or other tubular shaped body organ for treating conditions such as, for example, occlusions, stenoses, aneurysms, dissections, or weakened, diseased, or abnormally dilated vessels or vessel walls, by expanding the vessels or by reinforcing the vessel walls. Once delivered, the stents can be expanded using one or more inflatable members such as balloons. Stents can improve angioplasty results by preventing elastic recoil and remodeling of the vessel wall and treating dissections in blood vessel walls caused by balloon angioplasty of coronary arteries. Stents can also be used as a drug delivery medium for treatment of damaged portions of a vessel.

While conventional stent technology is relatively well developed, stent technologies related to treatment of the region of a vessel bifurcation are still being developed.

SUMMARY OF THE DISCLOSURE

The present disclosure relates to catheter assemblies adapted for use in treating a vessel bifurcation. The catheter assembly can include a main balloon, a branch balloon arrangement and a stent. The branch balloon arrangement can include a branch balloon and at least one orientation indicator. The orientation indicator can include visible markings on portions of the side balloon or on inflation segments coupled in fluid communication to the side balloon. The side balloon can have a specific color that is different from a color of the main balloon for improved visualization of the side balloon. The orientation indicator can be helpful in aligning the side balloon relative to features of the stent. The stent can include a side branch opening located between distal and proximal open ends of the stent. Aligning the side balloon axially and radially relative to the side branch opening of the stent can have implications in proper treatment of the vessel bifurcation using the catheter assembly.

There is no requirement that an arrangement include all features characterized herein to obtain some advantage according to this disclosure.

BRIEF DESCRIPTION OF THE DRAWINGS

FIG. 1 is a schematic side view of an example main catheter branch of a catheter assembly in accordance with principles of the present disclosure with the main and side balloons in an inflated state.

FIG. 2 is a schematic side view of the main catheter branch shown in FIG. 1 with the main and side balloons in a deflated state.

FIG. 3 is a top view of an example stent in accordance with principles of the present disclosure.

FIG. 4 is a schematic side view of an example catheter assembly in accordance with principles of the present disclosure that includes the main catheter branch of FIG. 1 and the stent of FIG. 3.

FIG. 5 is a schematic side view of the example catheter assembly shown in FIG. 4 positioned at a vessel bifurcation.

FIG. 6 is a schematic side view of a side balloon arrangement prepared for compression of the side balloon.

FIG. 7 is a schematic side view of an example main catheter branch with the side balloon in an alternative compressed state.

FIG. 8 is a schematic top view of the main catheter branch shown in FIG. 7.

FIGS. 9-13 are schematic top views of a side balloon arrangement with various marker arrangements.

FIG. 14 is a schematic side view of an example balloon arrangement according to principles of the present disclosure that includes a main balloon and an integral side balloon, wherein the main and side balloons are in an inflated state.

FIG. 15 is a schematic top view of the balloon arrangement shown in FIG. 14 and further including an example marker arrangement.

DETAILED DESCRIPTION

This disclosure relates to bifurcation treatment systems, catheter assemblies, and related methods of treating bifurcations in a patient's body. The term bifurcation means a division location from one unit into two or more units. Generally, two types of bifurcations of a body organ include: 1) a main tubular member defining a main lumen and a branch tubular member defining a branch lumen that extends or branches off from the main tubular member, wherein the main and branch lumens are in fluid communication with each other, and 2) a primary or main member defining a primary or main lumen (also referred to as a parent lumen) that splits into first and second branch members defining first and second branch lumens. The term lumen means the cavity or bore of a tubular structure such as a tubular organ (e.g., a blood vessel).

An example bifurcation is a vessel bifurcation that includes a continuous main vessel and a branch vessel, wherein the vessels define a main lumen and a branch lumen, respectively that are in fluid communication with each other. Alternatively, a vessel bifurcation can include a parent vessel that divides into first and second branch vessels, wherein the vessels define a parent lumen and first and second branch lumens, respectively, which lumens are all in fluid communication with each other.

Example applications of the inventive principles disclosed herein include cardiac, coronary, renal, peripheral vascular, gastrointestinal, pulmonary, urinary, and neurovascular systems. The catheter assemblies, systems and methods disclosed herein can be used for locating a branch vessel of the vessel bifurcation and for placement of a stent relative to the vessel bifurcation for treatment of the vessel bifurcation.

The main catheter branch 12 includes a catheter shaft 30, a main guidewire housing 32, a main balloon 34, and a side balloon arrangement 36. The main guidewire housing 32 extends at least partially within an internal lumen defined by the catheter shaft 30, and extends distally beyond the catheter shaft 30. The main guidewire housing 32 is sized to advance over a main guidewire 18. A spacing between the interior of the catheter shaft 30 and the main guidewire housing 32 defines an inflation lumen for delivering inflation fluid to the main and side balloons 34, 36.

The main balloon 34 includes a distal end portion 40, and a proximal end portion 42. The distal end portion 40 is secured to the main guidewire housing 32 at a location distal of the main balloon 34. The proximal end portion 42 is connected to the catheter shaft 30 at a location proximal of the main balloon 34.

The side balloon arrangement 36 includes a side balloon 50, a distal inflation segment 52, a proximal inflation segment 54, and a marker arrangement (described in further detail below with reference to at least FIGS. 9-13) that serves as an orientation indicator during assembly of the catheter assembly. A proximal end of the distal inflation segment 52 is connected in fluid communication with the side balloon 50. A distal end of the distal inflation segment 52 is connected to the distal end portion 40 of the main balloon 34 or to the main guidewire housing 32 at a location distal of the main balloon 34. A distal end of the proximal inflation segment 54 is connected in fluid communication with the side balloon 50. A proximal end of the proximal inflation segment 54 is connected to a proximal end portion 42 of the main balloon 34 or to the catheter shaft 34 at a location proximal the main balloon 34 so as to be in fluid communication with main balloon 34 and the inflation lumen defined by the catheter shaft 30. The side balloon 50 can additionally have a top surface 56 (see FIG. 6), first and second side portions 58, 59 (see FIG. 7), and a contact area 57 (see FIGS. 7 and 8) as will be described in further detail below.

The stent 16 includes a distal open end portion 60, a proximal open end portion 62, a side branch aperture 64 positioned at a location between the distal and the proximal open end 60, 62, and a plurality of expandable portions 66 (see FIG. 3) that define the side branch apertures 64. The expandable portions 66 can be referred to as pedals or crown points. Some example stent designs that include expandable portions are described in U.S. Pat. No. 7,118,593, which is incorporated herein by reference.

Typically, the expandable portions 66 are configured to move radially outward toward an extended position that substantially perpendicular to a central longitudinal axis of the stent 16 upon inflation of the side balloon 50. Further movement of the expandable portion 66 into the radial outward orientation can be provided by passing a post dilation balloon (not shown) through the side branch aperture 64 in a later step after removal of the main and side catheter branches 12, 14 from the stent 16.

The catheter assembly 10 is assembled by first advancing the main catheter branch 12 through an interior of the stent 16 such that the main balloon 34 spans both the distal and proximal open end portions 60, 62. The main catheter branch 12 is moved axially and radially (rotationally) to align the side balloon 50 with the side branch aperture 64. With the side balloon 50 aligned with the side branch aperture 64, the side catheter branch 14 is advanced through the stent to a position protruding through the proximal open end portion 62 and out of the side branch aperture 64. The stent 16 is then crimped onto the main and side catheter branches 12, 14. Crimping the stent helps maintain the catheter branches 12, 14 assembled with the stent 16 until inflation of at least one of the balloons 34, 50. Crimping the stent 16 can also reduce an outer profile of the catheter assembly 10 to a minimum size for improved ease in advancing the catheter assembly through a patient's vessels to a vessel bifurcation treatment site.

Referring to FIG. 5, the assembled catheter assembly 10 can be used to treat a vessel bifurcation 22. An initial step of treating the vessel bifurcation 22 is to advance a main guidewire 18 into a main vessel 24 of the vessel bifurcation, and advance a branch guidewire 20 into a branch vessel 26 of the vessel bifurcation. The catheter assembly 10 is advanced over the main and branch guidewires 18, 20 to the vessel bifurcation 22. In other treatment methods, the guidewires 18, 20 can be advanced into position in the vessels 24, 26 before or after the other, or in differing order relative to advancement of the catheter assembly 10 to a location adjacent the vessel bifurcation 22.

Distally advancing the catheter assembly 10 will advance a distal end portion 15 of the side catheter branch 14 into the branch vessel 26. Positioning the distal end portion 15 within the branch vessel 26 helps to align the side branch aperture 64 of the stent 16 radially relative to an ostium or opening 28 into the branch vessel 26. The catheter assembly 10 is advanced distally until the side branch aperture 64 is also positioned axially in alignment with the ostium 28. A plurality of markers 90 can be positioned along the main and side catheter branches 12, 14 to help in visually aligning the catheter assembly 10 relative to the vessel bifurcation 22 using visual techniques such as fluoroscopy.

Expanding the stent 16 into engagement with the vessel bifurcation 22 typically first includes expanding the main balloon 34 to expand the stent 16 into engagement with the main vessel 24 while the side branch aperture 64 is aligned with the ostium 28 of the branch vessel 26. The side balloon 50 typically inflates subsequent to inflation of the main balloon 34 even when the main balloon 34 and side balloon 50 are connected in fluid communication. Inflation of the side balloon 50 expands the expandable portion 66 of the stent 16 through the ostium 28 and towards the walls of the branch vessel 26. In some arrangements, the expandable portions 66 engage the side wall of the branch vessel 26 for treatment of the vessel bifurcation 22 in the area of the ostium 28.

Any misalignment of the side balloon 50 relative to the side branch aperture 64 during assembly of the catheter assembly 10 can result in movement of the expandable portion 66 in a non-symmetrical or uneven way relative to the ostium 28 of the branch vessel 26. Such non-symmetrical or uneven movement of the expandable portion 66 can hinder proper treatment of the vessel bifurcation 22, or at a minimum provide less optimum deployment of the stent 16 at the vessel bifurcation 22. Proper alignment and positioning of the main catheter branch 12 relative to the stent 16, in particular axial and radial alignment of the side balloon 50 relative to the side branch aperture 64, can influence successful operability of the catheter assembly 10 when treating a vessel bifurcation 22. The balloon orientation indicators described in further detail below can assist in such alignment during assembly of the catheter assembly 10.

The main and side balloons 34, 36 are typically formed from a length of hollow, tubular catheter material (see list of example catheter materials below). This stock catheter material is positioned in a balloon mold where heat and pressure are applied to expand portions of the stock catheter material into a desired balloon shape (e.g., the shape of main balloon 34 or the shape of side balloon 36).

Prior to assembling the main catheter branch 12 with the stent 16, the main balloon 34 and side balloon 50 can be compressed, folded, or otherwise arranged when in a deflated state to meet certain inflation objectives. For example, the main balloon 34 can be folded in such a way that limits rotation of the main balloon 34 relative to the stent 16 during inflation of the main balloon. The side balloon 50 can be provided in a deflated arrangement that promotes even and optimized movement of the expandable portion 66 of the stent 16 into the radial outward position. FIGS. 6-8 illustrate an example configuration and method of preparing a side balloon 50 prior to assembling the main catheter branch 12 with the stent 16.

FIG. 6 illustrates the side balloon arrangement 36 with the side balloon 50 in an inflated state. A balloon compressing member 68 arranged perpendicular to a central axis passing through the distal and proximal inflation segments 52, 54 can move down into engagement with a top surface 56 of the side balloon 50 in the direction Z to compress a side balloon 50. Concurrent with movement of the balloon compressing member 68 in a direction Z into engagement with the side balloon 50, a vacuum pressure condition can be applied interior of the side balloon arrangement 36 to help further compress the side balloon 50.

In some instances, the side balloon 50 will have opposing first and second side portions 58, 59 (see FIG. 8) that drape over the main balloon 34 in the assembly of the main catheter branch 12. A contact area 57 shown in FIGS. 7 and 8 illustrates where the balloon compressing member 68 may contact the top surface 56 to compress the side balloon 50. In other arrangements, the first and second side portions 58, 59 or other folds or flaps of the compressed side balloon 50 can be folded into a folding arrangement rather than permitting the side balloon 50 to drape over the main balloon 34 as shown in FIGS. 7 and 8. Draping of the side portions 58, 59 over the main balloon 34 is different from the schematically illustrated deflated side balloon 50 shown in FIGS. 2, 4, and 5.

The type and color of material used for each of the main and side balloons 34, 36 are typically the same to promote improved bonding of the distal and proximal inflation segments 52, 54 to the distal and proximal end portions 40, 42 of the main balloon 34. The preferred color for the stock catheter material is typically a clear or transparent material. A material that is clear or transparent can be considered having a clear or transparent color or colorant in accordance with the present disclosure. In contrast, the material of the side catheter branch 14 is colored so that the main and side catheter branches 12, 14 can be distinguished during assembly. In some instances, the material of the main and side catheter branches 12, 14 has the same color as well as the same material composition.

When the material used for the main and side balloons 34, 36 is the same, it can be difficult, in particular due to the relatively small size of the side balloon 50, to visually align the side balloon 50 with the side branch aperture 64 of the stent 16 during assembly of the catheter assembly 10. By adding a different colorant to the side balloon arrangement 36, in particular the side balloon 50, it can be easier for the assembler to visually see the position of the side balloon 50 relative to the main balloon 34 and the side branch aperture 64. In one example, the main balloon 34 comprises a material that has a clear or transparent colorant whereas the side balloon 50 comprises a different colorant such as blue, green, yellow, or red. The colorant of the side balloon 50 provides a distinct contrast in colors between the main balloon 34 and the side balloon 50.

Providing a colorant in the distal and proximal inflation segments 52, 54 can also influence ease in aligning the side balloon 50 relative to the side branch aperture 64 at least in the radial direction. Thus, a difference in colorant of the main balloon 34 and side balloon arrangement 36 can provide an orientation indicator for use in the assembly of catheter assembly 10. A difference in colors of the various portions of the catheter assembly 10 can also be defined as a marking or visual indicator for use in aligning features relative to each other during assembly of the catheter assembly 10.

Another way of providing an orientation indicator for the side balloon arrangement 36 is to add at least one marker arrangement (also referred to herein as markings), such as one of the marker arrangements 70A-E, 80A-E, 82A-E shown in FIGS. 9-13. The marker arrangements 70A-E, 80A-E, 82A-E are arranged and configured to be visible to the assembler of catheter assembly 10 during assembly of the catheter assembly 10.

The balloon markers 70A-E are positioned on the side balloon 50, for example, on the top surface 56 of the side balloon 50. In other arrangements, any one of the markers 70A-E or a portion of the markers 70A-E is positioned along a side, distal or proximal surface of the side balloon 50. Some example shapes for balloon markers are a plus (+), a cross (x), one or more dots (•), a circle (○), and a square shape (□). Many other shapes and sizes for the markers are possible. Providing at least one of the balloon markers 70A-E, preferably centrally located on the top surface 56, can help the assembler of the catheter assembly 10 identify a central point on the side balloon 50 that can be aligned with a central point of the side branch aperture 64 of the stent 16.

FIGS. 9-13 also illustrate a plurality of example inflation segment markers 80A-E, 82A-E. The markers 80A-E, 82A-E are arranged at least partially on the distal and proximal inflation segments 52, 54, respectively. The inflation segment markers 80A-E, 82A-E can be helpful in identifying for the assembler the proximal and distal sides of the side balloon 50, and also identifying the location of the distal and proximal inflation segments 52, 54 relative to the side balloon 50. The inflation segments 52, 54 can help in aligning the side balloon 50 both axially and radially relative to the side branch opening 64 of the stent 16.

Some example shapes for the inflation segment markers 80A-E, 82A-E include a band (80A, 82A) that at least partially extends around a circumference of the inflation segments 52, 54, plus (+), a cross (x), one or more dots (•), a circle (○), and a square shape (□) similar to those markers 70A-E shown in FIGS. 9-13.

In some arrangements, only a single one of the markers 80A-E or 82A-E is used in the side balloon arrangement 36. Alternatively, one of the markers 80A-E or 82A-E is used with one of the balloon markers 82A-E. Alternatively, a pair of markers 80A-E, 82A-E is provided without a balloon marker 70A-E. In any arrangement, different shaped markers can be used in combination for the markers 70A-E, 80A-E, 82A-E. Thus, any combination number and shapes of markers 70A-E, 80A-E, 82A-E can be used for a single side balloon arrangement 36.

There are many additional marker shapes, sizes, combinations of numbers of markers, shapes and sizes that are possible for providing at least one orientation indicator on the side balloon arrangement 36.

Referring now to FIGS. 14-15, an alternative balloon arrangement is shown and described. The balloon arrangement includes a main balloon 134 and a side balloon 150. The side balloon 150 is positioned at a location between distal and proximal end portions 140, 142 of the main balloon 134.

FIG. 15 illustrates a plurality of markers 170, 180, 182 positioned on the side and main balloons 134, 150. The markers 170, 180, 182 alone or in any combination provide orientation indicators for help in aligning the side balloon 150 relative to a side branch aperture of a stent (e.g., stent 16 described with reference to FIGS. 3-5). The markers 170, 180, 182 shown in FIG. 15 are plus (+) shaped. In other arrangements, any one of the markers 170, 180, 182 can have a different shape or size, such as those shapes described above with reference to FIGS. 9-13. Additional markers can be added at various locations on the main and side balloons 134, 150 to supplement the three markers shown in FIG. 15. In other arrangements, any of the markers 170, 180, 182 can be removed or repositioned at different locations relative to the main balloon 134.

The side balloon 150 can be integrally formed with the main balloon 134. Alternatively, the side balloon 150 can be formed as a separate piece that is later secured or otherwise mounted to the main balloon 134 in a separate step. The side balloon 150 can be compressed, folded, or otherwise prepared for assembly with a stent using the same or similar compression techniques and other features described with reference to FIGS. 6-8.

At least a portion of the material that defines the side balloon 150 can also have a different color than the material of the main balloon 134. The colorant of the side balloon 150 can be integral with the material composition. Alternatively, the colorant can be a coating that covers portions of the side balloon 150. In still further arrangements, the main balloon includes a colorant while the side balloon is void of a colorant, thus making the side balloon 150 visually distinctive from the main balloon 134.

Other types of balloon arrangements suited for treatment of a vessel bifurcation can benefit from the orientation indicators described above with reference to FIGS. 1-15.

Prior to assembling the main catheter branch 12 with the stent 16, the main balloon 34 and side balloon 50 can be compressed, folded, or otherwise arranged when in a deflated state to meet certain inflation objectives. For example, the main balloon 34 can be folded in such a way that limits rotation of the main balloon 34 relative to the stent 16 during inflation of the main balloon. The side balloon 50 can be provided in a deflated arrangement that promotes even and optimized movement of the expandable portion 66 of the stent 16 into the radial outward position. FIGS. 6-8 illustrate an example configuration and method of preparing a side balloon 50 prior to assembling the main catheter branch 12 with the stent 16.

FIG. 6 illustrates the side balloon arrangement 36 with the side balloon 50 in an inflated state. A balloon compressing member 68 arranged perpendicular to a central axis passing through the distal and proximal inflation segments 52, 54 can move down into engagement with a top surface 56 of the side balloon 50 in the direction Z to compress a side balloon 50. Concurrent with movement of the balloon compressing member 68 in a direction Z into engagement with the side balloon 50, a vacuum pressure condition can be applied interior of the side balloon arrangement 36 to help further compress the side balloon 50. In some instances, the side balloon 50 will have opposing first and second side portions 58, 59 (see FIG. 8) that drape over the main balloon 34 in the assembly of the main catheter branch 12. A contact area 57 shown in FIGS. 7 and 8 illustrates where the balloon compressing member 68 may contact the top surface 56 to compress the side balloon 50. In other arrangements, the first and second side portions 58, 59 or other folds or flaps of the compressed side balloon 50 can be folded into a folding arrangement rather than permitting the side balloon 50 to drape over the main balloon 34 as shown in FIGS. 7 and 8. Draping of the side portions 58, 59 over the main balloon 34 is different from the schematically illustrated deflated side balloon 50 shown in FIGS. 2, 4, and 5.

Materials and Other Considerations

The materials used in the balloons, catheter shafts, and edge protect members disclosed herein can be made of any suitable material including, for example, thermoplastic polymers, polyethylene (high density, low density, intermediate density, linear low density), various co-polymers and blends of polyethylene, ionomers, polyesters, polycarbonates, polyamides, poly-vinyl chloride, acrylonitrile-butadiene-styrene copolymers, polyether-polyester copolymers, and poly-etherpolyamide copolymers. One suitable material is Surlyn®, a copolymer polyolefin material (DuPont de Nemours, Wilmington, Del.). Still further suitable materials include thermoplastic polymers and thermoset polymeric materials, poly(ethylene terephthalate) (commonly referred to as PET), thermoplastic polyamide, polyphenylene sulfides, polypropylene. Some other example materials include polyurethanes and block copolymers, such as polyamide-polyether block copolymers or amide-tetramethylene glycol copolymers. Additional examples include the PEBAX® (a polyamide/polyether/polyester block copolymer) family of polymers, e.g., PEBAX® 70D, 72D, 2533, 5533, 6333, 7033, or 7233 (available from Elf AtoChem, Philadelphia, Pa.). Other examples include nylons, such as aliphatic nylons, for example, Vestamid L2101 IF, Nylon 11 (Elf Atochem), Nylon 6 (Allied Signal), Nylon 6/10 (BASF), Nylon 6/12 (Ashley Polymers), or Nylon 12. Additional examples of nylons include aromatic nylons, such as Grivory (EMS) and Nylon MXD-6. Other nylons and/or combinations of nylons can also be used. Still further examples include polybutylene terephthalate (PBT), such as CELANEX® (available from Ticona, Summit, N.J.), polyester/ether block copolymers such as ARNITEL® (available from DSM, Erionspilla, Ind.), e.g., ARNITEL® EM740, aromatic amides such as Trogamid (PA6-3-T, Degussa), and thermoplastic elastomers such as HYTREL® (Dupont de Nemours, Wilmington, Del.). In some embodiments, the PEBAX®, HYTREL®, and ARNITEL® materials have a Shore D hardness of about 45D to about 82D. The balloon materials can be used pure or as blends. For example, a blend may include a PBT and one or more PBT thermoplastic elastomers, such as RITEFLEX® (available from Ticona), ARNITEL®, or HYTREL®, or polyethylene terephthalate (PET) and a thermoplastic elastomer, such as a PBT thermoplastic elastomer. Additional examples of balloon material can be found in U.S. Pat. No. 6,146,356. It should be understood that the specific materials disclosed below for the individual embodiments does not limit the embodiment to those materials.

In the example catheter assemblies described above, some of the features can include a lubricious coating on an exterior surface thereof. The coating can promote insertion of the branch balloon into the branch vessel of a vessel bifurcation. The coating can also improve removal of the branch balloon from the branch vessel and the branch aperture of the stent when deflating and removing the catheter assembly from the vessel bifurcation after expansion of the stent. Some example coating for use with the branch balloon include hydrophilic polymers such as polyarylene oxides, polyvinylpyrolidones, polyvinylalcohols, hydroxyl alkyl cellulosics, algins, saccharides, caprolactones, and the like, and mixtures and combinations thereof. Hydrophilic polymers can be blended among themselves or with formulated amounts of water insoluble compounds (including some polymers) to yield coating with suitable lubricity, bonding and solubility. In some examples, portions of the devices described herein can be coated with a hydrophilic polymer or a fluoropolymer such as polytetrafluoroethylene (PTFE), better known as TEFLON®.

While the example stent delivery systems described above illustrate a balloon expandable stent having a predetermined side opening (i.e., branch aperture), other types of stents can be used with the catheter features described above. A variety of stents can be used with the systems and methods disclosed herein. Examples of such stents can be found in, for example, in U.S. Pat. Nos. 6,210,429; 6,325,826; and 7,220,275 the entire contents of which are incorporated herein by reference. In general, the aforementioned stents have a tubular shape with a continuous sidewall that extends between the proximal and distal ends. Proximal and distal stent apertures are defined at respective proximal and distal ends of the stent. A branch aperture is defined in the sidewall of the stent. The branch aperture provides access between an interior of the stent and an exterior of the stent. In some stents, the branch aperture includes expandable structure around a peripheral edge thereof that expands in a generally radial outward direction relative to a longitudinal axis of the stent. The expandable structure can be configured to extend into the branch lumen of the bifurcation upon expansion of the stent. The stent includes a plurality of strut structures that define the sidewall. The struts are expandable from a first, unexpanded state to a second, expanded state. Typically, the stent is configured to maintain the expanded state. The struts define a plurality of cell openings or cells along a length of the stent. The size and shape of the cells is typically different than the size and shape of the branch aperture. The stent is typically expanded once the stent is properly positioned in the main lumen of the bifurcation with the branch aperture aligned radially and axially with an opening into the branch lumen. The stent, including the expandable structure surrounding the branch aperture, can be expanded with a single expansion or with multiple expansions using, for example, one or more inflatable balloons.

Conclusion

One aspect of the present disclosure relates to a catheter assembly that includes a stent and a main catheter branch. The stent includes a distal open end, a proximal open end, and a side branch aperture. The side branch aperture is positioned at a location between the distal and proximal open ends. The main catheter branch includes a catheter shaft, a main guidewire housing, a main balloon and a side balloon. The main balloon has a proximal end portion and distal end portion. The side balloon is positioned at a location between the proximal and distal end portions of the main balloon and extends radially outward relative to the main balloon when inflated. The side balloon includes at least one orientation indicator configured for orientation of the side balloon relative to the side branch aperture of the stent. The at least one orientation indicator can be a difference in colorant of at least a portion of the side balloon from a colorant of the main balloon. The at least one orientation indicator can also be a marking positioned on a surface of the side balloon.

Another aspect of the present disclosure relates to a catheter balloon assembly adapted for use with a stent. The stent includes a side branch opening that is positioned at a location between opposing open ends of the stent. The assembly includes a main balloon and a side balloon. The main balloon has opposing proximal and distal end portions. The side balloon is positioned at a location between the proximal and distal end portions of the main balloon and includes at least one orientation indicator. The at least one orientation indicator is configured for alignment of the side balloon relative to the side branch opening of the stent.

A still further aspect of the present disclosure relates to a method of assembling a catheter assembly. The catheter assembly includes a main balloon, a side balloon, and a stent. The main balloon includes opposing proximal and distal end portions. The side balloon is positioned at a location between the proximal and distal end portions of the main balloon and is configured to extend radially outward relative to the main balloon when inflated. The side balloon includes at least one orientation indicator. The stent includes a side branch opening positioned at a location between a distal open end and a proximal open end of the stent. The method steps include providing the main balloon and the side balloon in a deflated state, positioning at least a portion of the main balloon and the side balloon within an interior of the stent, and aligning the side balloon with the side branch opening of the stent using the at least one orientation indicator.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A catheter assembly, comprising:
(a) a stent, the stent having a distal open end, a proximal open end, and a side branch aperture, the side branch aperture positioned at a location between the distal and proximal open ends; and
(b) a main catheter branch, the main catheter branch including:
   i. a catheter shaft;
   ii. a main guidewire housing;
   iii. a main balloon having a proximal end portion and a distal end portion; and
   iv. a side balloon positioned at a location between the proximal and distal end portions of the main balloon and extending radially outward relative to a top surface of the main balloon when inflated, the side balloon being in fluid communication with the main catheter branch through a proximal inflation segment and a distal inflation segment, the side balloon including two or more separate orientation indicators configured for orientation of the side balloon relative to the side branch aperture of the stent during assembly, wherein the two or more separate orientation indicators include a first assembly marking positioned centrally only on a top surface of the side balloon, wherein the top surface of the side balloon is on an opposite side of the side balloon from a bottom surface that faces the top surface of the main balloon, and at least a second assembly marking on one of the proximal and distal inflation segments adjacent the side balloon, wherein the two or more separate orientation indicators include a colorant of the side balloon that is different from a colorant of the main balloon, wherein the first and second assembly markings are located on the side balloon and inflation segment, respectively, such that the markings are viewable through the side branch aperture on the stent from above the top surface of the side balloon when the side balloon is positioned over the main balloon and the main and side balloons are positioned inside the stent during assembly of the catheter, wherein the colorant of the orientation indicators and the colorant of the main balloon are distinguishable by an individual during assembly.

2. The catheter assembly of claim 1, further comprising a side catheter branch, the side catheter branch defining a branch guidewire housing, the side catheter branch extending through the proximal open end of the stent and out of the side branch opening of the stent.

3. The catheter assembly of claim 1, wherein at least one of the two or more separate orientation indicators has a shape selected from the group comprising: + (plus), x (cross), • (dot), and □ (square).

4. The catheter assembly of claim 1, wherein the side balloon is formed integral with the main balloon.

5. The catheter assembly of claim 1, wherein the two or more separate orientation indicators are formed using at least one of the group comprising: laser marking, micro inking, mandrel etching, material addition, or mold marks in a mold used to form the side balloon.

6. The catheter balloon assembly of claim 1, wherein the colorant of the main balloon is transparent.

7. The catheter balloon assembly of claim 6, wherein the colorant of the at least one orientation indicator is selected from the group consisting of blue, green, yellow, and red.

8. A catheter balloon assembly adapted for use with a stent, the stent having a side branch opening positioned at a location between opposing open ends of the stent, the assembly comprising:
(a) a main balloon, the main balloon having opposing proximal and distal end portions; and
(b) a side balloon arrangement including a side balloon positioned at a location between the proximal and distal end portions of the main balloon, the side balloon arrangement including a distal inflation segment and a proximal inflation segment, the distal and proximal inflation segments being coupled in fluid communication with the side balloon at distal and proximal sides of the side balloon, respectively, the side balloon arrangement including two or more orientation indicators configured for alignment of the side balloon relative to the side branch opening of the stent, wherein the two or more orientation indicators include a first assembly marker disposed centrally on only a top surface of the side balloon away from the main balloon, the first assembly marker positioned to allow visual identification of a central point on the top surface of the side balloon by an individual assembling the catheter balloon assembly, and at least a second assembly marker disposed on one of the distal and proximal inflation segments adjacent the side balloon, wherein the two or more orientation indicators include a colorant that is different from a colorant of the main balloon, wherein the two or more orientation indicators are different shapes, wherein the first and second assembly markers are viewable through the side branch opening in the stent from above the top surface of the side balloon during assembly of the catheter balloon assembly.

9. The catheter balloon assembly of claim 8, wherein the side balloon is integral with the main balloon.

10. The catheter balloon assembly of claim 8, wherein at least one of the proximal and distal inflation segments includes at least one orientation indicator that is a colorant that is different from the colorant of the main balloon.

* * * * *